United States Patent [19]
Asgharian et al.

[11] Patent Number: 6,139,794
[45] Date of Patent: Oct. 31, 2000

[54] METHODS OF STERILIZING POLYMERS

[75] Inventors: Bahram Asgharian; Alok K. Kulshreshtha, both of Arlington, Tex.

[73] Assignee: Alcon Laboratories, Inc., Fort Worth, Tex.

[21] Appl. No.: 09/123,772

[22] Filed: Jul. 28, 1998

Related U.S. Application Data

[60] Provisional application No. 60/054,119, Jul. 29, 1997.

[51] Int. Cl.[7] ............................ A61L 11/00; A61L 2/00
[52] U.S. Cl. .............................. 422/1; 422/28; 422/34; 422/38
[58] Field of Search .................................. 422/1, 28, 34, 422/292, 307, 901, 38

[56] References Cited

U.S. PATENT DOCUMENTS

| | | | |
|---|---|---|---|
| 4,407,791 | 10/1983 | Stark . | |
| 4,525,346 | 6/1985 | Stark . | |
| 4,585,654 | 4/1986 | Landaburu et al. | 422/1 |
| 4,758,595 | 7/1988 | Ogunbiyi et al. . | |
| 4,836,986 | 6/1989 | Ogunbiyi et al. . | |
| 5,599,863 | 2/1997 | Zimmerman | 524/308 |

*Primary Examiner*—Krisanne Thornton
*Attorney, Agent, or Firm*—Michael C. Mayo

[57] ABSTRACT

Methods of heat sterilizing polymers are disclosed. The methods involve the preparation of a polymer suspension in an water-miscible organic liquid and subsequent application of moderate heat for a period of time sufficient to sterilize the polymer.

15 Claims, No Drawings

METHODS OF STERILIZING POLYMERS

The present application claims priority to U.S. provisional Ser. No. 60/054,119 filed Jul. 29, 1997.

BACKGROUND OF THE INVENTION

The present invention relates to the sterile preparation of polymers. More specifically, the present invention relates to moderate heat sterilization of polymers, and preferably, heat-labile polymers. The methods of the present invention involve the formation of suspension comprising a water-miscible organic liquid and a polymer, followed by subsequent heat sterilization.

Polymers are used extensively in the preparation of food, medical and pharmaceutical compositions. The type of polymer used will depend on the functional needs of a given composition. For example, if viscosity enhancement is required, polymers providing viscosity enhancing effects, such as polyvinyl alcohol, polyvinyl pyrrolidone, various cellulosic polymers such as carboxymethyl cellulose or hydroxypropylmethyl cellulose, may be used. If a surfactant is required, surfactants such as polaxamines, polaxamers, alkyl ethoxylates or others may be used. If a gelling polymer is required, polymers such as gellan, carageenan or carbomers may be used.

Certain preparations of food, medical or pharmaceutical compositions require the employment of sterilization methods in order to eliminate microbial contamination. Various methods of polymer sterilization have been available in the art. For example, techniques of filter sterilization can be used. Such methods usually involve the filtration of the composition, partial formulation or individual ingredients of the compositions, wherein such components are passed through a filter with a pore size too small for microbes to pass through. Autoclaving, another method of sterilization, involves the steam heat and pressure treatment of a composition, or individual components of the composition, for a given time to effect the elimination of microbes. Other methods of sterilization involve the irradiation of the composition, or individual components, with particle/energy rays such as gamma rays or electron beams. Still other methods of sterilization involve the dry heat treatment of the polymers.

Although the foregoing methods of sterilization are useful for numerous polymers, certain polymers require more complicated steps of sterilization. For example, if certain composition or components are too viscous or comprise polymers or particles that are too large to pass through the pores of a filter, then filter sterilization will not be useful. If certain compositions or individual components are hydrolytically unstable, then autoclaving methods will not be effective. Although dry heat sterilization techniques may provide an alternative to polymers susceptible to autoclaving hydrolysis, there are still some polymers which degredate or otherwise lose cross-linking ability during dry heat treatments. Additionally, some compositions may comprise components that present a variety of sterilization problems which make the sterile preparation of such compositions possible, using conventional techniques, but labor and cost prohibitive. Therefore, what is needed are new methods of sterilization which provide effective sterilization of polymers, and especially, difficult to sterilize polymers, thereby providing a labor/cost improvement over the prior art methods.

SUMMARY OF THE INVENTION

The present invention relates to the preparation of sterile polymers. More specifically, the present invention relates to moderate heat sterilization methods of polymers and especially heat-labile polymers. The methods involve the dispersion of the polymers in a water-miscible organic liquid and subsequent moderate heat treatment of the suspension to sterilize the polymer.

The addition of such organic liquids provides a more homogeneous and effective heat transfer to the polymer suspension. Additionally, less oxidation of the polymer occurs due to the limited supply and access of oxygen to the polymer, as compared to dry heat sterilization. Thus, one object of the present invention is to provide alternative methods of sterilization which allow for the moderate heat sterilization of otherwise heat-labile polymers, with minimal effects on polymer properties.

DETAILED DESCRIPTION OF THE INVENTION

The methods of the present invention involve the suspension of a polymer in a water-miscible organic liquid and the subsequent heat sterilization of the mixture. As used herein, "water-miscible organic liquid," "organic liquid" or "stabilizer" refers to a pharmaceutically acceptable organic compound that forms one liquid phase with water when added to water. As stated above, the addition of the organic molecule to the polymer effects greater heat transfer and protection of the polymer from oxidation. The particular structure of the organic molecule is generally not an important factor in effective sterilization of the polymer. It is rather the ability of the organic liquid to form one phase with water, and the safety of the organic liquid, that determines its stabilizing utility. Additionally, the stabilizers must also be suitable for consumer use and will thus exhibit minimal adverse effects with consumer use. Preferably, the stabilizers will be compatible for ophthalmic use. For example, the stabilizer will not contribute to ocular irritation/toxicity or interfere with the anti-microbial efficacy of an anti-microbial agent. Given the above criteria, various and numerous molecules may be used in the present invention to stabilize the polymer during sterilization methods of the present invention.

As used herein, "heat-labile polymer" refers to polymers that undergo hydrolysis or and/or oxidation following standard autoclaving or dry heat sterilization temperatures. Examples of heat-labile polymers are those which do not exhibit a cloud point. As used herein "sterilization" means the effective inactivation or kill of microbes contained in the polymer powder, mixture, suspension or solution. The level of inactivation or kill may vary, but it will be in amount acceptable by the applicable commercial and/or FDA standards for the intended product.

Preferred water-miscible organic liquids useful in the methods of the present invention include polyethylene glycols (PEGs), such as PEG 200, PEG 400, PEG 600; and glycerol, propylene glycol or mixtures thereof. The most preferred organic liquids are the PEGs, and most preferably, PEG 400.

The methods of the present involve the addition of the organic liquid to the polymer powder and subsequent heat sterilization of the suspension. In general, a 1:0.1 to 1:5 suspension of the organic liquid to the polymer is first prepared. The particular ratio will depend on various factors, such as the chemical nature of the polymer and the organic liquid. In general, such suspension preparation involves the dispersion of a polymer powder in an organic liquid with subsequent mixing. Particular parameters, i.e., mixing conditions, time and temperature, will vary depending on the polymer and organic liquid employed. In general, however, the polymer suspensions will typically be mixed for 15 minutes at room temperature.

The conditions for moderate heat sterilization will vary. In general, a temperature of about 110° to 150° C. and for a duration of about 0.5 to 8 hours will be employed. Preferred methods will employ temperatures of 125° C. and for a duration of 1 hour. Unlike autoclaving, the methods of the present invention do not involve the use of direct moisture and pressure application to the polymer. Rather, the methods of the present invention only employ moderate heat to a sealed, water vapor-proof vessel. Preferred methods involve the use of an autoclaving device to heat the sealed vessel. Following sterilization, the polymer mixture is then set aside for final mixing with any additional sterilized components.

Although the methods of the present invention can be used with any number of polymers, the methods are particularly suited for heat-labile polymers exhibiting high cloud point or no cloud point, such as galactomannan polysaccharides. Thus, methods of the present invention are most preferably employed to sterilize heat-labile polymers including guar gum, locust bean gum and tara gum.

The types of galactomannans that may be sterilized by the methods of the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Of particular interest are galactomannans made up of linear chains of $(1-4)$-$\beta$-D-mannopyranosyl units with $\alpha$-D-galactopyranosyl units attached by (1–6) linkages. The ratio of D-galactose to D-mannose varies, but generally will be from about 1:2 to 1:4. Galactomannans having a D-galactose:D-mannose ratio of about 1:2 are of greatest interest. Additionally, other chemically modified variations of the polysaccharides are also included in the "galactomannan" definition. For example, hydroxyethyl, hydroxypropyl and carboxymethylhydroxypropyl substitutions may be made to the galactomannans prior to sterilization. Still other non-ionic variations to the galactomannans, such as those containing alkoxy and alkyl (C1–C6) groups (e.g., hydroxylpropyl substitutions) may be sterilized by methods of the present invention. An example of non-ionic substitution of a galactomannan of the present invention is hydroxypropyl guar, which is preferably substituted up to about a 0.4 molar ratio.

The galactomannans may be obtained from numerous sources. Such sources include guar gum, locust bean gum and tara gum, as further described below. Additionally, the galactomannans may also be obtained by classical synthetic routes or may be obtained by chemical modification of naturally occurring galactomannans.

Guar gum is the ground endosperm of *Cyamopisis tetragonolobus* (L.) Taub. The water soluble fraction (85%) is called "guaran" (molecular weight of 220,000), which consists of linear chains of $(1-4)$-$\beta$-D mannopyranosyl units with $\alpha$-D-galactopyranosyl units attached by (1–6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum can be obtained, for example, from Rhone-Polulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, *ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

Modified galactomannans of various degree of substitution are commercially available from Rhone-Poulenc (Cranbury, N.J.). Hydroxypropyl guar with low molar substitution (e.g., less than 0.6) are of particular interest.

The polymer compositions to be sterilized by the methods of the present invention may contain other ingredients. Such ingredients include pharmaceuticals, carriers, antimicrobial/preservative agents, tonicity adjusting agents, buffers and chelating agents. Tonicity adjusting agents useful in the compositions of the present invention may include salts such as sodium chloride, potassium chloride and calcium chloride; non-ionic tonicity agents may include propylene glycol and glycerol; chelating agents may include EDTA and its salts; and pH adjusting agents may include hydrochloric acid, Tris, triethanolamine and sodium hydroxide. Suitable anti-microbial agents/preservatives are discussed more fully below. The above listing of examples is given for illustrative purposes and is not intended to be exhaustive. As stated above, the use of the methods of the presentation in the preparation of compositions for ophthalmic applications is of particular interest to the inventor. Thus, examples of other agents useful for the foregoing purposes are well known in contact lens care formulation and are contemplated by the present invention.

Disinfecting compositions to be sterilized by methods of the present invention will contain an antimicrobial agent. Antimicrobial agents may be either monomeric or polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB") or polyaminopropyl biguanide ("PAPB"), which are polymeric biguanides. These preferred antimicrobial agents are disclosed in U.S. Pat. Nos. 4,407,791 and 4,525,346, issued to Stark, and 4,758,595 and 4,836,986, issued to Ogunbiyi, respectively. The entire contents of the foregoing publications are hereby incorporated in the present specification by reference. Other antimicrobial agents suitable in the compositions and methods of the present invention include: other quaternary ammonium compounds, such as benzalkonium halides, and other biguanides, such as chlorhexidine. The antimicrobial agents used herein are preferably employed in the absence of mercury-containing compounds such as thimerosal. Particularly preferred antimicrobial agents of the present invention are polymeric quaternary ammonium compounds of the structure:

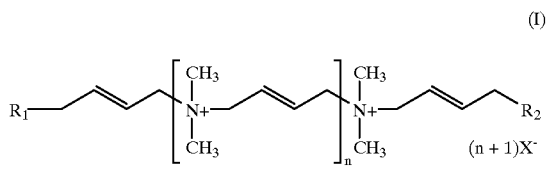

(I)

wherein:

R₁ and R₂ can be the same or different and are selected from:

$N^+(CH_2CH_2OH)_3X^-$, $N(CH_3)_2$ or OH;

X is a pharmaceutically acceptable anion, preferably chloride; and n=integer from 1 to 50. The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein X is chloride and R₁, R₂ and n are as defined above.

The polymers may be sterilized alone (that is, in the presence of the organic liquid) or in combination with any of the ingredients described above.

EXAMPLE 1

This example demonstrates the degradation susceptibility of galactomannans sterilized by typical autoclave cycles. A 0.5% weight/volume ("w/v") Guar gum was prepared and polish filtered to remove insoluble materials. The polymer solution was subjected to a 20, 30 or a 60 minute autoclave cycle. Following the autoclave cycle, the viscosity of the solution was measured and compared to the non-autoclaved solution. The effects of autoclaving the unprotected polymer are illustrated in Table 1:

TABLE 1

| Treatment | Viscosity (CPS) |
| --- | --- |
| Control | 399 |
| Post-autoclave 20 min. cycle | 39 |
| Post-autoclave 30 min. cycle | 18 |
| Post-autoclave 60 min. cycle | 5.9 |

Significant reduction in viscosity is observed even for a 20 minute cycle and the effect increases with longer cycle times.

EXAMPLE 2

This example demonstrates the sterilization efficacy of a method of the present invention as compared to other methods of sterilization. The comparison was made with Hydroxypropyl guar, a heat-labile polymer. Viscosity measurement were taken from a 0.5% w/v polymer solution which was prepared following each treatment. The preparation of the polymer for the present invention method (No. 1) and method No. 2 involved the addition of 1 gram of HP guar gum to 2 grams of PEG-400. All other methods used a standard dry powder of HP guar gum. The results are illustrated in Table 2:

TABLE 2

HP-Guar Polymer Sterilized with Various Methods

| No. | Treatment | Appearance | Viscosity (CPS) |
| --- | --- | --- | --- |
| 1 | Suspension of Gum in PEG (Present Invention) | Light Yellow powder in clear Solution | 255.6, 276.4 |
| 2 | Suspension of Gum in PBG Dry Heat, in Open Container | Light Brown in Slightly Yellow Solution | 115.6, 114.8 |
| 3 | Vacuum Dried followed by dry heat | Dark Brown Powder | 22.6, 21.7 |
| 4 | Dry Heat | Dark Brown Powder | 48.7, 49.0 |
| 5 | Dry Heat under N₂ | Dark Brown Powder | 21.2, 22.9 |
| 6 | Unsterilized Gum (control) | Light Yellow Powder | 278.2, 278.4 |

Minimal depolymerization was observed with the present invention method (No. 1), as compared to the other methods employed. Additionally, there was no change in physical appearance of the polymer using the method of present invention, in contrast to the prior art methods. This observation may show that limited oxidation occurred through the present invention method.

EXAMPLE 3

This example illustrates a method of the sterile preparation a multi-purpose, contact lens care solution using a method of the present invention:

| Ingredient | Concentration (% W/V) | Amount per 20 liters |
| --- | --- | --- |
| Hydroxypropyl Guar Gum | 0.20 | 40 g |
| Polyethylene Glycol 400 | 0.40 | 80 g |
| Tetronic 1304 | 0.25 | 50 g |
| Boric Acid | 1.00 | 200 g |
| Propylene Glycol | 0.90 | 180 g |
| Disodium Edetate | 0.01 | 2 g |
| Polyquaternium-1 | 0.001 + 50% Excess | 0.3 g (100%) |
| Sodium Hydroxide and/or Hydrochloric Acid | adjust pH (6.8–7.2) (target 7.0) | n/a |
| Purified Water | QS 100% | QS 20 liters or 20.06 kg |

Preliminarily, a compounding vessel (20 L stainless steel pressure can), a 0.2 micron sterilizing filter, a receiving vessel (20 L carboy), a 4.5 micron polishing filter, a 0.2 micron sterilizing filter, a vent filter, and the filling equipment are sterilized by autoclaving.

In a beaker equipped with an overhead agitator, add the weighed amount of polyethylene glycol 400 (200 g). While mixing slowly disperse the weighed amount of hydroxypropyl ("HP") Guar gum (100 g). Mix until completely homogeneous. In a 500 ml Schott bottle, equipped with a magnetic stir bar, weigh exactly 120.0 g of the HPGuar gum/PEG-400 dispersion. Prepare to sterilize by autoclaving. In a second identical 500 ml Schott bottle weigh exactly 120.0 g of the same dispersion. Prepare to use as a dummy during the autoclaving cycle. To both bottles add 1.3 ml of purified water (amount equivalent, by volume, of the microorganism suspension used to inoculate the bottles during the validation study). Mix both bottles for 10 minutes using a magnetic stir plate. Autoclave the HPGuar gum/PEG-400 dispersion using the validated time-temperature cycle of 80 minutes at 125° C.

In a vessel equipped with an overhead agitator, add purified water equivalent to approximately 70% of the theoretical batch weight (approximately 14 Kg). While mixing at moderate speed, slowly add the other ingredients desired: Tetronic 1304, Boric Acid, Propylene Glycol, and Disodium Edetate. Mix for a minimum of 60 minutes, or until completely homogeneous. Check the temperature and, if necessary, cool to 35° C. or below. While mixing at low speed slowly add the Polyquaternium-1. Mix for a minimum of 15 minutes, or until completely homogeneous. Transfer into a pre-sterilized compounding vessel equipped with an agitator through a 0.2 micron sterilizing filter (the recommended compounding vessel is a pressure vessel and recommended agitator is an overhead mixer that can be used in sterile compounding area). Rinse the vessel and filter assembly with room temperature WFI.

Aseptically transfer the sterilized HPGuar gun/PEG-400 dispersion into the pre-sterilized compounding vessel. Rinse the bottle content with sterilized purified water. Bring the content of the compounding vessel to exactly 95% of the theoretical batch weight (19.0 liters or 19.06 Kg) using sterile room temperature purified water. Allow the HPGuar gum/PEG slurry to hydrate while mixing, at moderate speed, in the compounding vessel for a minimum of 2 hours. Transfer the contents of the compounding vessel through a 4.5 micron pre-sterilized polishing filter into the pre-sterilized receiving vessel equipped with a stir bar. There will be some loss of the contents due to the product held in filter housing and filter cartridge. Check and adjust pH, if necessary, to 6.9–7.1 (target 7.0) using 1N NaOH or 1N HCl. Approximately 3–4 ml of 1N NaOH per 1 liter of final batch weight is needed to achieve the desired pH. QS to final batch weight using sterile purified water. Mix at low speed for a minimum of 30 minutes.

EXAMPLE 4

The sterilization efficacy of the methods of the present invention were tested in the following microbial challenge assay:
The following stock solutions and suspensions were prepared:
1. Three 0.12 kg suspensions of HP guar comprised of 40 g of HP guar and 80 g of PEG-400 were prepared by dispersing dry polymer powder into PEG-400 and mixing to prepare a homogeneous suspension for each of the studies below. The mixing time was about 15–30 minutes.
Study 1 and 2:
2. Spore suspension (40%) ethanol—*Bacillus stearothermophilus* ATCC 12980 (AMSCO SPORDEX®) label count $1.3 \times 10^7$ CFU/0.1 mL and a $D_{121}$ Value of 1.7 minutes.
3. Spore suspension (40%) ethanol—*Bacillus subtilis* var. *niger* ATCC 9372 (AMSCO SPORDEX®) label count $1.2 \times 10^7$ CFU/0.1 mL and a D121 Value of 1.3 minutes.
Study 3:
4. Spore suspension (40%) ethanol—*Bacillus stearothermophilus* ATCC 12980 (AMSCO SPORDEX(®) label count $1.4 \times 10^7$ CFU/0.1 mL and a $D_{121}$ Value of 1.6 minutes.
5. Spore suspension (40%) ethanol—*Bacillus subtilis* var. *niger* ATCC 9372 (AMSCO SPORDEX®) label count $1.1 \times 10^7$ CFU/0.1 mL and a D121 Value of 1.3 minutes.
120 gram aliquots of the HP guar/PEG-400 suspension were placed in 500 mL screw cap media bottles with a stir bar. Each of two test suspensions were inoculated with *Bacillus stearothermophilus* spores to attain approximately $10^6$ CFU/mL of test suspension. Two additional containers of test suspension were inoculated with *Bacillus subtilis* var. *niger* spores to attain approximately $10^6$ CFU/mL of test suspension. (Study 1: *Bacillus stearothermophilus*, $1.9 \times 10^6$ CFU/mL of test suspension or $1.6 \times 10^8$ CFU/bottle; *Bacillus subtilis* var. *niger*, $2.6 \times 10^6$ CFU/mL of test suspension or $2.6 \times 10^8$ CFU/bottle; Study 2: *Bacillus stearothermophilus*, $1.7 \times 10^6$ CFU/mL of test suspension or $1.5 \times 10^8$ CFU/bottle; *Bacillus subtilis* var. *niger*, $3.2 \times 10^6$ CFU/mL of test suspension or $3.0 \times 10^8$ CFU/bottle; Study 3: *Bacillus stearothermophilus*, $1.8 \times 10^6$ CFU/mL of test suspension or $1.7 \times 10^8$ CFU/bottle; *Bacillus subtilis* var. *niger*, $4.3 \times 10^6$ CFU/mL of test suspension or $3.9 \times 10^8$ CFU/bottle.)

Samples were placed on magnetic stir plates and the contents allowed to stir for a minimum of 10 minutes. One container inoculated with *Bacillus stearothermophilus* and one container inoculated with *Bacillus subtilis* var. *niger* were then placed in an autoclave device for an autoclave cycle of 40 minutes at 125° C. One container inoculated with *Bacillus stearothermophilus* and one container inoculated with *Bacillus subtilis* var. *niger* were maintained as controls. Following the treatment (or control) cycle, aliquots of each set of suspensions were serially diluted and then mixed with trypticase soy agar (TSA). The *Bacillus stearothermophilus* plates were wrapped in parafilm to prevent desiccation and incubated for 55°–60° C. for 48–72 hours (controls) or 7 days (experimentals). The *Bacillus subtilis* var. *niger* were incubated at 30°–35° C. for 48–72 hours (controls) or 7 days (experimentals). Following the incubation period, each plate was examined microscopically for growth. Table 3 illustrates the total kill effect of the heat sterilization methods of the present invention on the test HP guar suspension:

TABLE 3

| Study No. | Log Reduction | | | |
| | *Bacillus stearothermophilus* | | *Bacillus subtilis* var. *niger* | |
| | per mL | per bottle | per mL | per bottle |
|---|---|---|---|---|
| 1 | 6.3 | 8.2 | 6.4 | 8.4 |
| 2 | 6.2 | 8.2 | 6.5 | 8.5 |
| 3 | 6.3 | 8.2 | 6.6 | 8.6 |

What is claimed is:

1. A method of sterilizing a polymer which comprises the steps of:
   dispersing the polymer in a water-miscible organic liquid;
   mixing the polymer and organic liquid to form a polymer/organic liquid suspension;
   placing the suspension in a sealed, water-vapor proof vessel; and
   heating the suspension for a period of time effective to sterilize the polymer.

2. A method according to claim 1, wherein the suspension is heated at a temperature of from 110° to 150° C. for a period of from 0.5 to 8 hours.

3. A method according to claim 1, wherein the polymer is a heat-labile polymer.

4. A method according to claim 3, wherein the heat-labile polymer is a galactomannan polymer.

5. A method according to claim 4, wherein the galactomannan is selected from the group consisting of guar, tara and locust bean gum.

6. A method according to claim 4, wherein the galactomannan polymer is HP-guar.

7. A method according to claim 1, wherein the water-miscible organic liquid is a polyethylene glycol.

8. A method according to claim 7, wherein the polyethylene glycol is selected from the group consisting of PEG 200, PEG 400 and PEG 600.

9. A method according to claim 1, wherein the polymer is a galactomannan and the water-miscible organic liquid is a polyethylene glycol.

10. A method according to claim 9, wherein the galactomannan is HP-guar and the polyethylene glycol is PEG-400.

11. A method according to claim 1, wherein the suspension is heated at a temperature of 125° C. for a duration of at least 40 minutes.

12. A method according to claim 9, wherein the suspension is heated at a temperature of 125° C. for a duration of at least 40 minutes.

13. A method according to claim 10, wherein the suspension is heated at a temperature of 125° for a duration of at least 40 minutes.

14. A method of preparing a sterile composition containing a polymer comprising the steps of:

sterilizing the polymer by:
      dispersing the polymer in a water-miscible organic liquid;
      mixing the polymer and organic liquid to form a polymer/organic liquid suspension;
      placing the suspension in a sealed, water-vapor proof vessel; and
      heating the suspension for a period of time effective to sterilize the polymer; and
   mixing the sterilized polymer suspension with pre-sterilized excipients to form a sterile composition containing a polymer.

15. A method according to claim 14, wherein the composition comprises:

about 0.20% w/v hydroxypropyl guar gum;
   about 0.40% w/v polyethylene glycol 400;
   about 0.25% w/v tetronic 1304;
   about 1.00% w/v boric acid;
   about 0.90% w/v propylene glycol;
   about 0.01% w/v disodium Edetate; and
   about 0.0015% w/v polyquaternium-1;
   wherein the composition is adjusted to a pH of from 6.5 to 7.5 with sodium hydroxide and hydrochloric acid.

* * * * *